United States Patent [19]

Stucky et al.

[11] Patent Number: 5,693,800

[45] Date of Patent: Dec. 2, 1997

[54] N-(2-AMINO-4,6-DICHLOROPYRIMIDINE-5-YL) FORMAMIDE AND A PROCESS FOR ITS PREPARATION

[75] Inventors: Gerhard Stucky; René Imwinkelried, both of Brig-Glis, Switzerland

[73] Assignee: Lonza AG, Basel, Switzerland

[21] Appl. No.: 693,521

[22] Filed: Aug. 8, 1996

Related U.S. Application Data

[62] Division of Ser. No. 428,916, Apr. 25, 1995, Pat. No. 5,583,226.

[30] Foreign Application Priority Data

Apr. 27, 1994 [CH] Switzerland .................. 01299/94

[51] Int. Cl.$^6$ .................................................. C07D 239/48
[52] U.S. Cl. .................................. 544/322; 544/330
[58] Field of Search ................................. 544/322, 330

[56] References Cited

U.S. PATENT DOCUMENTS 5,294,710 3/1994 Stucky et al. ..................... 544/320

FOREIGN PATENT DOCUMENTS

| 0552758 | 7/1993 | European Pat. Off. . |
| 0684236 | 11/1995 | European Pat. Off. . |
| 9101310 | 2/1991 | WIPO . |

OTHER PUBLICATIONS

M. Legraverend et al., "A New Route to 2,5–Diamino–4, 6–dichloropyrimidine . . . ", *Synthesis*, vol. 7 (1990), pp. 587–589.

C. Temple, Jr. et al., "Preparation of . . . ", *Journal of Organic Chemistry*, vol. 40 (1975), pp. 3141–3142.

C. Temple, Jr. et al., "Preparation of . . . ", *Chemical Abstracts*, vol. 89 (1978), p. 591, Abstract No. 215347s.

*Primary Examiner*—Yogendra N. Gupta
*Attorney, Agent, or Firm*—Brumbaugh, Graves, Donohue & Raymond

[57] ABSTRACT

A novel pyrimidine derivative, N-(2-amino-4,6-dichloropyrimidine-5-yl)formamide for use, e.g., in the production of antiviral nucleotide derivatives, can be made by a process involving cyclyzing an aminomalonic ester with guanidine or its salt in the presence of a base to produce 2,5-diamino-4,6-dihydroxypyrimidine or its salt, chlorinating this product with a chlorinating agent in the presence of an amide to produce 4,6-dichloropyrimidine, and reacting the 4,6-dichloropyrimidine with an aqueous solution of a carboxylic acid to produce the N-(2-amino-4,6-dichloropyrimidine-5-yl)formamide. Novel also are 4,6-dichloropyrimidine, 4,6-dichloro-N'-(dimethylaminomethylene)pyrimidine-2,5-diamine, 4,6-dichloro-N'-(piperidine-1-ylmethylene)pyrimidine-2,5-diamine, and a process for making 2,5-diamino-4,6-dichloropyrimidine of the formula

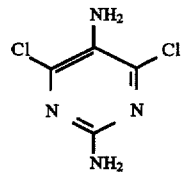

VII

1 Claim, No Drawings

N-(2-AMINO-4,6-DICHLOROPYRIMIDINE-5-YL) FORMAMIDE AND A PROCESS FOR ITS PREPARATION

This application is a division of application Ser. No. 08/428,916, filed on Apr. 25, 1995, now U.S. Pat. No. 5,583,226.

BACKGROUND OF THE INVENTION

The invention relates to pyrimidine derivatives, for use, e.g., as intermediates in the preparation of antiviral nucleotide derivatives.

Preparation of antiviral nucleotide derivatives is described, e.g., in International Publication WO-91/01310. Known as intermediates in the preparation of antiviral nucleotide derivatives are N-5-protected 2,5-diamino-4,6-dichloropyrimidines as disclosed in European Patent Document EP-A-0552758, for example. However, these compounds suffer from the disadvantage that they are difficult to convert into the corresponding nucleotide derivatives.

SUMMARY OF THE INVENTION

It is an object of the invention to provide a pyrimidine derivative which can be used to obtain the corresponding nucleotide derivatives with good yield, and to provide a commercially advantageous process for preparing the pyrimidine derivative.

Preferred in these respects is a novel pyrimidine derivative designated as N-(2-amino-4,6-dichloropyrimidine-5-yl) formamide of the formula

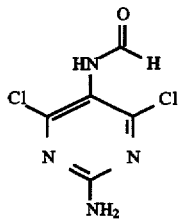

I

A preferred process for making N-(2-amino-4,6-dichloropyrimidine-5-yl)formamide comprises the steps of (a) cyclyzing an aminomalonic ester with guanidine or its salt in the presence of a base to produce 2,5-diamino-4,6-dihydroxypyrimidine or its salt, (b) chlorinating this product with a chlorinating agent in the presence of an amide to produce 4,6-dichloropyrimidine, and (c) reacting the 4,6-dichloropyrimidine with an aqueous solution of a carboxylic acid to produce the N-(2-amino-4,6-dichloropyrimidine-5-yl)formamide.

DETAILED DESCRIPTION

In step (a), an aminomalonic ester of the general formula

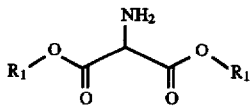

II where $R_1$ denotes a $C_1$-$C_6$-alkyl group or its salt, is cyclized with guanidine or its salt in the presence of a base to give 2,5-diamino-4,6-dihydroxypyrimidine of the formula

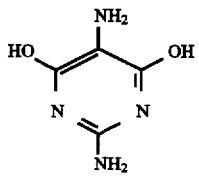

III or its salt. The aminomalonic esters of the general formula II which are employed as starting compounds may be obtained in well-known manner by amidating the corresponding malonic ester derivatives.

An alkali metal alcoholate, such as, e.g., sodium or potassium methoxide, or sodium or potassium ethoxide, is conveniently used as the base, in conformity with EP-A-0552758. In-situ-formed sodium methoxide in methanol or sodium ethoxide in ethanol is preferably employed.

Conveniently used as the salts of the aminomalonic ester and of guanidine are their hydrochloride or hydrobromide salts.

The cyclization is conveniently carried out at a temperature of between room temperature and the reflux temperature of the relevant solvent, preferably at the reflux temperature.

After a customary reaction time of between 2 and 6 h, the intermediate of the formula III can then be isolated where appropriate, using customary methods of preparation. The synthesis of the end product of the formula I is preferably carried out without isolating the intermediate of the formula III.

Step (b) is carried out by chlorinating the intermediate of the formula III, or its salt, with a chlorinating agent in the presence of an amide of the general formula

IV to form a 4,6-dichloropyrimidine of the general formula

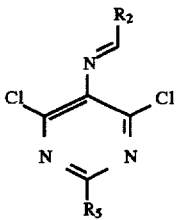

V

The substituent $R_5$ denotes —$NH_2$. The substituent $R_2$ denotes either (i) a 5- or 6-membered heterocycloalkyl radical which is optionally substituted on the heteroatom, such as, e.g., piperidinyl, morpholinyl, thiomorpholinyl, pyrrolidinyl or N-methylpiperazinyl, preferably piperidinyl or pyrrolidinyl, or (ii) $NR_3R_4$, where $R_3$ and $R_4$ are identical or different and are each a $C_1$-$C_6$-alkyl group, such as, e.g., methyl, ethyl, propyl, isopropyl, butyl, pentyl or hexyl, preferably methyl, or a benzyl group.

Thus, N,N-dimethylformamide, N,N-diethylformamide, N,N-diisopropylformamide, N-formylpiperidine, N-formylmorpholine, N-formylthiomorpholine, N,N-methylformylpiperazine or N,N-dibenzylformamide, preferably N,N-dimethylformamide, N-formylpiperidine or N,N-dibenzylformamide may be employed as amides of the formula IV.

The salts of the intermediate of the formula III which are conveniently used are its hydrochloride or hydrobromide salts, or its alkali metal salts, such as, e.g., its sodium or potassium salt.

The chlorinating agents which may be employed are those which are familiar to those skilled in the art, such as, e.g., phosphorus oxychloride, thionyl chloride, sulphuryl chloride, phosphorus trichloride, phosphorus pentachloride, phosgene or diphosgene. Phosphorus oxychloride is preferably used as the chlorinating agent.

The chlorinating agent and the amide (IV) are conveniently employed in a molar ratio of from 1-to-0.55 up to 1-to-10, preferably in a molar ratio of from 1-to-0.55 up to 1-to-1.

Chlorination is conveniently carried out at a temperature of from 50° C. up to the reflux temperature of the relevant solvent.

The above-described amide can be employed as the solvent for chlorination. Additionally, chlorination can be carried out with an inert solvent. Examples of suitable inert solvents are toluene, xylene, chloroform, dichloromethane, dichloroethane or chlorobenzene, preferably toluene or dichloroethane.

Following a customary reaction time of from 3 to 24 h, the corresponding 4,6-dichloropyrimidine of the general formula V (with $R_5$=—$NH_2$) can be isolated in a manner familiar to those skilled in the art. These 4,6-dichloropyrimidine intermediates in the preparation of N-(2-amino-4,6-dichloropyrimidine-5-yl)formamide are novel in themselves and are a part of the invention. 4,6-dichloro-N'-(dimethylaminomethylene)pyrimidine-2,5-diamine and 4,6-dichloro-N'-(piperidine-1-ylmethylene)pyrimidine-2,5-diamine 5 are preferred representatives of the 4,6-dichloropyrimidines (V, with $R_5$=—$NH_2$).

Precursors of these 4,6-dichloropyrimidines (V) may also be isolated in dependence on the selected reaction conditions or working-up conditions. These precursors are likewise defined by the general formula V. $R_5$ then denotes —NH—CH=O or —N=CH—$R_2$, where $R_2$ is as specified above. These precursors, as novel intermediates in the preparation of N-(2-amino-4,6-dichloropyrimidine-5-yl)formamide, are novel in themselves and are a part of the invention. 4,6-dichloro-N,N'-bis(dimethylaminomethylene)pyrimidine-2,5-diamine, 4,6-dichloro-N,N'-bis(piperidine-1-ylmethylene) pyrimidine-2,5-diamine or N-[4,6-dichloro-5-(dimethylaminomethyleneamino) pyrimidine-2-yl] formamide are preferred representatives.

In step (c), the 4,6-dichloropyrimidines of the general formula V are reacted with an aqueous solution of a carboxylic acid of the general formula

$R_6$—COOH         VI where $R_6$ denotes a $C_1$-$C_6$-alkyl group, branched or unbranched, or a $C_3$-$C_6$-cycloalkyl group, to give the end product of the formula I.

Acetic acid, propionic acid, butyric acid, pentanoic acid, hexanoic acid, isobutyric acid, pivalic acid, cyclopropanecarboxylic acid, cyclopentanecarboxylic acid, or cyclohexanecarboxylic acid may be employed as the carboxylic acid. Use of acetic acid, propionic acid or pivalic acid is particularly convenient.

Carboxylic acid is conveniently employed at a concentration of from 20 to 70 vol.%, preferably of from 25 to 50 vol.%.

It was found that, if the carboxylic acid in step (c) is employed in an aqueous alcoholic solution, 2,5-diamino-4,6-dichloropyrimidine of the formula VII is formed directly. This compound can also be converted into the corresponding nucleotide derivative. Accordingly, the process for preparing 2,5-diamino-4,6-dichloropyrimidine of the formula

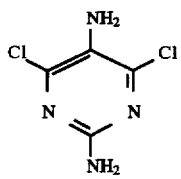

VII is also a part of the invention.

An aqueous solution of methanol, ethanol, propanol, butanol, pentanol or hexanol may be employed as the aqueous alcoholic solution.

The reaction in step (c) is conveniently carried out at a temperature of from 50° to 100° C., preferably at a temperature of from 70° to 90° C.

Following a customary reaction time of from 1 to 10 h, the end product of the formula I or VII can be isolated using working-up methods which are familiar to those skilled in the art. As contrasted with the previously known N-5-protected 2,5-diamino-4,6-dichloropyrimidines (EP-A-0552758), the novel end product of the formula I, and also the previously known end product of the formula VII, can be converted readily and with good yield into the corresponding nucleotide derivative.

EXAMPLE 1

Preparation of N-(2-amino-4,6-dichloropyrimidine-5-yl)formamide 1.1 Preparation of 4,6-dichloro-N'-(dimethylaminomethylene)pyrimidine-2,5-diamine One-pot process:

A suspension of 25 g (117 mmol) of aminomalonic ester hydrochloride in 50 ml of methanol was cooled down to 10° C., and 21.07 g of sodium methoxide (30% in methanol) was added. This suspension was added drop-wise to a mixture of 63.2 g (351 mmol) of sodium methoxide (30% solution in methanol) and 12.55 g (128.7 mmol) of guanidine hydrochloride in 50 ml of methanol. The reaction mixture was heated to reflux and then stirred at this temperature for 16 hours. Subsequently, 13.5 g (370 mmol) of HCl gas was passed into the warm suspension. The methanol was then distilled off. During the distillation, a total of 200 ml of toluene was slowly added drop-wise. After all the methanol had been distilled out, 71.6 g (468 mmol) of $POCl_3$ was added drop-wise, followed by 34.2 g (468 mmol) of dimethylformamide, which was added drop-wise at 80° C. The mixture was left to stir at 80° C. for 17.5 hours and then cooled down to room temperature; 64.7 g of $K_2CO_3$, dissolved in 150 ml of water, was then added slowly. The mixture was heated once again at 50° C. for 5 hours. The mixture was then adjusted to a pH of 7 using a 30% solution of NaOH, cooled, and the product was filtered off. After washing with water and drying in vacuo, 23.2 g (85%) of pure product was obtained as a pale brown solid. $^1$H—NMR (DMSO, 400 MHz)δ: 2.9–3.0 (2s, 6H); 6.9 (s, 2H); 7.6 (s, 1H). $^{13}$C—NMR (DMSO, 100 MHz): 33.5; 39.3; 130.3; 153.5; 157.0; 157.1. m.p.: 195° C. (decomp.).

1.2 Preparation of N-(2-amino-4,6-dichloropyrimidine-5-yl) formamide (i) A solution of 2.35 g (10 mmol) of the product from 1.1 above, in 15 g of a 50% aqueous solution of propionic acid, was stirred at 70° C. for 7 hours. The mixture was then cooled down and the product filtered off. After washing with water and drying in vacuo, 1.66 g of a white solid was obtained. This solid was suspended in 50 ml of a 2M solution of $K_2CO_3$ and the suspension was stirred at room temperature for 2 hours. The suspension was filtered and the product was washed with water and dried in vacuo. 1.33 g (64%) of pure product was obtained as an almost white solid. $^1$H—NMR (DMSO, 300 MHz)δ: 9.6–10.1 (b, 1H); 8.3 and 8.0 (2s, 1H); 7.7 and 7.6 (2s, 2H).

(ii) Proceeding in analogy with (i) above, pivalic acid was employed as the carboxylic acid in place of propionic acid, and the product was worked up in a corresponding manner. The yield was 70%.

EXAMPLE 2

Preparation of 4,6-dichloro-N'-(dimethylaminomethylene)pyrimidine-2,5-diamine 2.1 Preparation of 4,6-dichloro-N,N'-bis(dimethylaminomethylene)pyrimidine-2,5-diamine A suspension of 4.46 g (25 mmol) of diaminodihydroxypyrimidine hydrochloride in 45 ml of toluene and 15.33 g (100 mmol) of phosphorus oxychloride was heated to 90° C. 7.31 g (100 mmol) of dimethylformamide was added dropwise within a span of 45 minutes. The mixture was then stirred at 90° C. for 20 hours. The reaction mixture was allowed to cool down, and 100 g of a 10% solution of $K_2CO_3$ was slowly added to it. 19.5 g of solid $K_2CO_3$ was then added so that the pH rose to 7. The product was extracted with three portions of ethyl acetate. The combined organic phases were dried over $MgSO_4$ and concentrated on a rotary evaporator. 6.44 g of a pale brown solid was obtained, corresponding to a yield of 89%. $^1$H—NMR (DMSO, 400 MHz)δ: 2.9–3.1 (4s, 12H); 7.6 (s, 1H); 8.5 (s, 1H). $^{13}$C—NMR (DMSO, 100 MHz): 33.5; 39.4; 40.4; 134.2; 153.0; 156.7; 158.0; 159.1. m.p.: 121.5°–123° C. CHN: calculated for $C_{10}H_{14}Cl_2N_6$: C 41.54, H 4.88, N 29.06; found: C 41.4, H 4.58, N 28.6.

2.2 Preparation of N-[4,6-dichloro-5-(dimethylaminomethyleneamino)pyrimidine-2-yl]formamide A suspension of 3 g (10 mmol) of the product from 2.1 above, in 10 ml of a 50% aqueous solution of acetic acid, was stirred at room temperature for 4.5 hours. The product was then filtered off and washed twice with 10 ml of water on each occasion. After drying in vacuo, 2.18 g (83%) of pure product was obtained as a white solid. $^1$H—NMR (DMSO, 400 MHz)δ: 2.9–3.1 (2s, 6H); 7.7 (s, 1H); 9.2 (d, 1H); 11.2 (d, 1H). $^{13}$C—NMR (DMSO, 100 MHz): 33.6; 39.6; 136.9; 149.6; 153.4; 156.9; 162.5. m.p.: 172.5°–174° C. CHN: calculated for $C_8H_9Cl_2N_5$: C 36.66, H 3.46, N 26.72; found: C 36.7, H 3.07, N 25.9.

2.3 Preparation of 4,6-dichloro-N'-(dimethylaminomethylene)pyrimidine-2,5-diamine A solution of 1.85 g (7.1 mmol) of the product from 2.2 above, in 25 ml of 10% hydrochloric acid, was heated to 40° C. and stirred at this temperature for 1.5 hours. The reaction mixture was cooled down and the pH was adjusted to 8.7 with 2M $K_2CO_3$. The product, which had precipitated out, was filtered off and washed with water. After drying in vacuo, 1.52 g (91%) of pure product was obtained as a white solid.

The spectroscopic data were analogous to those given above.

2.4 Preparation of 4,6-dichloro-N'-(dimethylaminomethylene)pyrimidine-2,5-diamine
One-pot process:

A suspension of 4.46 g (25 mmol) of diaminodihydroxypyrimidine hydrochloride in 90 ml of toluene and 15.33 g (100 mmol) of phosphorus oxychloride was heated to 80° C. 7.31 g (100 mmol) of dimethylformamide was added dropwise within a span of 60 minutes. The reaction mixture was then stirred at 80° C. for 16 hours. It was allowed to cool down, and 100 ml of water was then added. The pH was adjusted to 10 using a total of 8.4 g of $Na_2CO_3$. The reaction mixture was heated to 40° C. and stirred at this temperature for 4 hours. It was then cooled down to room temperature and neutralized with a 30% solution of NaOH, and the product was filtered off. After washing with water and drying in vacuo, 5.5 g (95%) of product was obtained as a beige solid. This corresponds to a yield of 89%.

The spectroscopic data were analogous to those given above.

EXAMPLE 3

Preparation of 4,6-dichloro-N'-piperidine-1-ylmethylene)pyrimidine-2,5-diamine 3.1 Preparation of 4,6-dichloro-N,N'-bis(piperidine-1-ylmethylene)pyrimidine-2,5-diamine A suspension of 3.57 g (20 mmol) of diaminodihydroxypyrimidine hydrochloride in 70 ml of toluene and 12.27 g (80 mmol of phosphorus oxychloride was heated to 80° C. 9.05 g (80 mmol) of 1-formylpiperidine was added dropwise within a span of 60 minutes. The reaction mixture was then stirred at 80° C. for 22 hours. It was allowed to cool down, and 100 ml of a 1M solution of $K_2CO_3$ was then added to it. The pH was then adjusted to 7 with NaOH. The product was extracted with three portions of ethyl acetate. The combined organic phases were dried over $MgSO_4$ and concentrated on a rotary evaporator. 10.87 g of an oil was obtained which still contained a large quantity of N-formylpiperidine. The product was purified by suspending in hexane and then filtering. The yield was greater than 90%. $^1$H—NMR (DMSO, 300 MHz)δ: 8.5 (s, 1H); 7.7 (s, 1H); 3.4–3.8 (m, 8H); 1.5–1.9 (m, 12H).

3.2 Preparation of 4,6-dichloro-N'-(piperidine-1-ylmethylene)pyrimidine-2,5-diamine A solution of 9.9 g (18.2 mmol) of the product from 3.1 above, in 73 g of 10% HCl, was first stirred at room temperature for 4.5 hours and then stirred at 47° C. for 2 hours. It was cooled down and the pH was adjusted to 7 using 30% NaOH. The product was filtered off, washed with water and dried in vacuo. 4.68 g (88%) of product was obtained as a pale brown solid. $^1$H—NMR (DMSO, 300 MHz)δ: 7.55 (s, 1H); 7.4 (s, 2H); 3.2–3.7 (m, 4H); 1.5–1.8 (m, 6H).

EXAMPLE 4

Subsequent conversion of N-(2-amino-4,6-dichloropyrimidine-5-yl) formamide into 2-amino-9-butyl-6-chloropurine 4.1 Preparation of N-(2-amino-4-butylamino-6-chloropyrimidine-5-yl)formamide A solution of 0.43 g (2 mmol) of N-(2-amino-4,6-dichloropyrimidine-5-yl)formamide and 0.31 g (4.2 mmol) of n-butylamine in 10 ml of tetrahydrofurane was stirred at room temperature for 17 hours. Water was then added to the reaction mixture and the product was extracted with ethyl acetate. After drying the organic phase over $MgSO_4$, and concentrating it on a rotary evaporator, 0.49 g of a white solid was obtained which was purified by recrystallizing in toluene. 0.46 g of pure product was obtained, corresponding to a quantitative yield. $^1$H—NMR (DMSO, 300 MHz)δ: 9.0 and 8.6 (s and d, 1H); 8.1 and 7.8 (s and d, 1H); 7.0 and 6.75 (2t, 1H); 6.5 and 6.4 (2s, 2H); 3.3–3.4 (m, 2H); 1.4–1.6 (m, 2H); 1.2–1.4 (m, 2H); 0.9 (t, 3H).

4.2 Preparation of 2-amino-9-butyl-6-chloropurine

A suspension of 0.51 g (2 mmol) of the product from 4.1 above, in 10 ml of diethoxymethyl acetate, was heated to reflux for 3.5 hours. It was then completely evaporated, and 30 ml of a 0.5M solution of HCl was added to the residue. After 3 hours at room temperature, the yellow solution was adjusted to a pH of 8 using NAOH, and the resulting suspension was extracted 3× with ethyl acetate. The combined organic phases were dried and concentrated on a rotary evaporator. 0.46 g (97%) was obtained of the desired product, which was 95% pure (according to $^1$H—NMR). $^1$H—NMR (DMSO, 300 MHz)δ: 8.2 (s, 1H); 6.9 (s, 2H); 4.05 (t, 2H); 1.6–1.9 (m, 2H); 1.1–1.4 (m, 2H); 0.9 (t, 3H).

4.3 Conversion of 5-(N-ethoxycarbonyl)-2-amino-4,6-dichloropyrimidine into 2-amino-9-butyl-6-chloro-7,9-dihydropurine-8-one (comparative example)

As a comparative example, 5-(N-ethoxycarbonyl)-2-amino-4,6-dichloropyrimidine, as a derivative of an N-5-protected 2,5-diamino-4,6-dichloropyrimidine (EP-A-0552758), was reacted under conditions which were analogous to those in Example 4.

However, under these conditions, 2-amino-9-butyl-6-chloro-7,9-dihydropurine-8-one was obtained rather than 2-amino-9-butyl-6-chloropurine.

EXAMPLE 5

Preparation of 2,5-diamino-4,6-dichloropyrimidine

A mixture of 2.35 g (10 mmol) of the product from Example 1.1 in 5 g of pivalic acid, 10 ml of methanol and 15 ml of water was stirred at 80° C. for 4.5 hours. The precipitated solid was subsequently filtered off and the filtrate was neutralized with a concentrated solution of NaOH. It was then extracted with ethyl acetate and the combined organic phases were dried over MgSO$_4$. Following concentration on a rotary evaporator, 1.40 g of a product mixture remained, 65% of which consisted of the desired product (for a yield of 51%) as determined by $^1$H—NMR. The product was not subjected to further purification.

EXAMPLE 6

Subsequent conversion of 2,5-diamino-4,6-dichloropyrimidine into 2-amino-9-butyl-6-chloropurine

6.1 2,5-diamino-4-butylamino-6-chloropyrimidine

A suspension of 2.5 g (14 mmol) of 2,5-diamino-4,6-dichloropyrimidine, 1.37 g (18.7 mmol) of n-butylamine and 6 ml of triethylamine in 60 ml of butanol was stirred at 100° C. for 9 hours. The reaction mixture was then cooled down and concentrated to dryness on a rotary evaporator. Water was added to the residue and the product was extracted with ethyl acetate. After the organic phase had been dried over Na$_2$SO$_4$ and concentrated on a rotary evaporator, the residue was suspended in 10 ml of isopropyl ether, and the product was filtered off and dried. 2.24 g (75%) of an orange-red solid was obtained. $^1$H—NMR (CDCl$_3$, 300 MHz)δ: 5.4 (broad s, 1H); 4.6 (s, 2H); 3.4 (t, 2H); 2.7 (s, 2H); 1.6 (m, 2H); 1.4 (m, 2H); 0.95 (t, 3H).

6.2 Preparation of 2-amino-9-butyl-6-chloropurine

A solution of 1.0 g (4.63 mmol) of the product from 6.1 above, in 10 ml of dimethylformamide and 10 ml of ethyl orthoformate, was cooled down to 0° C., and 0.5 ml of concentrated HCl was added. In conjunction with this, the temperature rose to 10° C. The mixture was then stirred at room temperature for 22 hours. It was then completely evaporated, and 40 ml of an 0.5M solution of HCl was added to the residue. After 2 hours at room temperature, the yellow solution was adjusted to a pH of 8 with NaOH, and the resulting suspension was extracted 3× with ethyl acetate. The combined organic phases were dried and concentrated on a rotary evaporator. 1.1 g (quantitative) was obtained of the desired product, which was 95% pure (by $^1$H—NMR).

The spectroscopic data were analogous to those in Example 4.2.

We claim:

1. A process for making 2,5-diamino-4,6-dichloropyrimidine of the formula

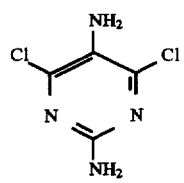

the process comprising:

(a) in a volume comprising aminomalonic ester of the formula

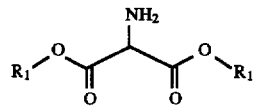

where R$_1$ is one of a C$_1$–C$_6$-alkyl group and its salt, cyclizing the aminomalonic ester with one of guanidine and its salt in the presence of a base, to produce an intermediate comprising one of 2,5-diamino-4,6-dihydroxypyrimidine of the formula

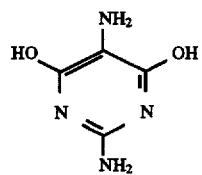

and its salt;

(b) in the intermediate, chlorinating the 2,5-diamino-4,6-dihydroxypyrimidine in the presence of an amide of the formula

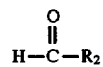

where is one of (i) a 5-membered heterocycloalkyl radical which is optionally substituted on the heteroatom, (ii) a 6-membered heterocycloalkyl radical which is optionally substituted on the heteroatom, (iii) —NR$_3$R$_3$, where R$_3$ is one of a C$_1$–C$_6$-alkyl group and a benzyl group, and (iv) —NR$_3$R$_4$, where R$_3$ and R$_4$ each are one of a C$_1$–C$_6$-alkyl group and a benzyl group, to produce a 4,6-dichloropyrimidine of the formula

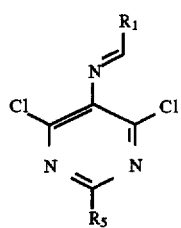 V
where $R_5$ is $-N_2$; and
(c) reacting the 4,6-dichloropyrimidine with a carboxylic acid of the formula
$$R_6\text{—COOH} \qquad \text{VI}$$
where $R_6$ is one of (i) a branched $C_1$–$C_6$-alkyl group, (ii) an unbranched $C_1$–$C_6$-alkyl group, and (iii) a $C_3$–$C_6$-cycloalkyl group, in an aqueous alcoholic solution, to produce the substance of the formula VII.
* * * * *